United States Patent [19]
Bales et al.

[11] Patent Number: 5,228,451
[45] Date of Patent: Jul. 20, 1993

[54] BIOPSY FORCEPS DEVICE HAVING STIFF DISTAL END

[75] Inventors: Thomas O. Bales; Matthew A. Palmer, both of Miami, Fla.; Jeff A. Wilson, Mendon, Mass.

[73] Assignee: Symbiosis Corporation, Miami, Fla.

[21] Appl. No.: 865,913

[22] Filed: Apr. 9, 1992

Related U.S. Application Data

[63] Continuation-in-part of Ser. No. 521,766, May 10, 1990, Pat. No. 5,133,727, and a continuation-in-part of Ser. No. 837,046, Feb. 18, 1992.

[51] Int. Cl.⁵ ............................................. A61B 10/00
[52] U.S. Cl. ................................... 128/751; 606/205
[58] Field of Search ............. 128/749, 751, 754, 757, 128/752, 753; 606/205, 206, 207, 208, 167, 170, 174

[56] References Cited

U.S. PATENT DOCUMENTS

| | | | |
|---|---|---|---|
| 4,721,116 | 1/1988 | Schintgen et al. | 128/751 |
| 4,763,668 | 8/1988 | Macek et al. | 128/751 |
| 4,815,460 | 3/1989 | Porat et al. | 606/207 |
| 4,880,015 | 11/1989 | Nierman | 128/751 |
| 4,887,612 | 12/1989 | Esser et al. | 128/751 |
| 4,907,598 | 3/1990 | Bauer | 128/753 |
| 5,035,248 | 7/1991 | Zinnecker | 128/751 |
| 5,082,000 | 1/1992 | Picha et al. | 128/751 |

Primary Examiner—Lee S. Cohen
Assistant Examiner—Samuel Gilbert
Attorney, Agent, or Firm—David P. Gordon

[57] ABSTRACT

A biological forceps device is disclosed for the taking of tissue samples from a body. The biopsy forceps device comprises a flexible main coil having a distal end which is stiffer than the majority of the coil, a pair of opposed jaws hingedly disposed on the distal end of the coil, and an actuator having a distal end coupled to the hingedly disposed jaws for effecting articulation of the jaws. Preferably, shrink wrap tubing is placed on the distal end of the coil and acts as the stiffening agent thereof. A stiffer distal end permits the practitioner to press the jaws deeper into the tissue and reduces the jump experienced at the distal end when the coils go from a state of tension (jaws open) to a state of compression (jaws closed), so that a better sample can be obtained.

20 Claims, 4 Drawing Sheets

BIOPSY FORCEPS DEVICE HAVING STIFF DISTAL END

This is a continuation-in-part of Ser. Nos. 07/521,766, filed May 10, 1990, now U.S. Pat. No. 5,133,727, and Ser. No. 07/837,046, filed Feb. 18, 1992, which are both hereby incorporated by reference herein in their entireties.

BACKGROUND OF THE INVENTION

This invention relates to biopsy forceps devices. More particularly, this invention relates to biopsy forceps devices having long coils, typically on the order of several feet long.

A number of different types of biopsy forceps are in common use, typically in conjunction with endoscopic assistance. Ordinarily, these devices are of complicated construction, requiring the manufacturing and machining of precise miniaturized components, which are therefore generally quite expensive. Examples of such biopsy forceps devices may be seen with reference to U.S. Pat. No. 3,895,636 to Schmidt, U.S. Pat. No. 4,669,471 to Hayashi, U.S. Pat. No. 4,721,116 to Schintgen et al., U.S. Pat. No. 4,763,668 to Macek et al., U.S. Pat. No. 4,815,476 to Clossik, U.S. Pat. No. 4,817,630 to Schintgen et al., U.S. Pat. No. 4,880,015 to Nierman, and U.S. Pat. No. 4,887,612 to Esser et al. Another device for taking cellular tissue is disclosed in U.S. Pat. No. 4,936,312 to Tsukagoshi. None of the aforereferenced patents disclose a device where the distal end of the coil of the biopsy forceps is stiffened relative to the remainder of the coil. In fact, U.S. Pat. No. 4,936,312 to Tsukagoshi suggests quite the opposite; i.e., that the distal end of the coil be loosened relative to the remainder of the coil by forming a more loosely wound coil with space between the coil elements.

SUMMARY OF THE INVENTION

The inventors hereof have determined that for devices which are designed to take cellular tissue, such as biopsy forceps devices, it is desirable that the distal end of the device be relatively stiff so that the jaws or other tissue taking element of the device does not jump when activated. The stiff distal end will permit the practitioner to press the jaws or other tissue taking element deeper into the tissue so that a better sample can be obtained. In addition, a stiff distal end will reduce the jump experienced at the distal end when the coils go from a state of tension (jaws open) to a state of compression (jaws closed).

It is therefore an object of the invention to provide a biopsy forceps device having a relatively stiffened distal end.

It is another object of the invention to provide a biopsy forceps device where the stiffening mechanism has advantageous properties which counteract the increased difficulty of bending the stiffened distal end.

It is a further object of the invention to provide a biopsy forceps device with a relatively stiffened distal end in conjunction with an advantageous jaw arrangement where the jaws are identical cast devices which self align to permit large manufacturing tolerances.

In accord with the objects of the invention, a biopsy forceps device is provided and comprises a flexible main coil having distal and proximal ends with the distal end being stiffer than a majority of the main coil, opposed first and second jaws disposed on the distal end of the main coil with at least one of the jaws being hingedly disposed, and actuation means for effecting articulation of the hingedly disposed jaw(s) where the distal end of the actuation means is coupled to the articulating jaw. Preferably, the distal end of the main coil is stiffened by providing a Teflon shrink wrap tubing thereabout. Because the Teflon shrink wrap is lubricious and smooth, the additional difficulty in guiding the slightly stiffer distal end of the biopsy forceps device down the endoscope is offset by the more slippery nature of shrink wrap coated distal end. While Teflon shrink wrapping of the entire main coil of a biopsy forceps device is known in the art, the purpose for such shrink wrap is for insulating a "hot" biopsy forceps device, and the wrapping of only a portion of the coil not only would be undesirable, but possibly dangerous.

A less preferred manner of stiffening the distal end of the coil is to splice a stiffer coil material to a less stiff coil material.

The present invention of a biopsy forceps having a coil with a stiffened distal end preferably utilizes a pair of jaws which are formed from a casting. Each jaw of the pair of jaws of the biopsy forceps may be a duplicate of the other jaw. Each jaw is somewhat hemispherically shaped having an elongated portion which extends proximally into a cutter tang. Each cutter jaw has a generally U-shaped distalmost end on which is defined a plurality of radially disposed teeth. The teeth on one side of the longitudinal centerline of the jaw are displaced by one-half pitch from the corresponding teeth on the other side of the longitudinal centerline on that jaw. The displacement by one-half pitch of the teeth on one side of the jaw relative to those corresponding teeth on the other longitudinal side of the jaw permits the same casting to be used for both the upper and lower jaws. The radially disposed array of teeth on each of the jaws permits a self-aligning feature therewith, thus compensating for the slightly looser tolerances found in the casting manufacturing technique.

Each jaw extends proximally and terminates in a tang, as aforementioned. Each tang is arranged so as to receive a joggled pull wire therethrough. Each jaw is mated with one another about a clevis pin which is cast unitarily with a clevis. The clevis extends into a housing which is crimped to a main coil, the proximal end of which extends into a handle having means for articulating the jaws. Each joggled pullwire from the tang on the proximal end of each jaw flexibly extends through the main coil and into the hub of the handle at the proximal end of the forceps assembly.

The handle comprises a central shaft about which a displaceable spool is disposed. The central shaft has a longitudinally directed stepped diameter bore extending therein on its distal end, and a thumb ring on its proximalmost end. The proximal end of the coil extends into the bore on the proximal end of the central shaft. The bore in the central shaft of the handle has a stepped configuration. The distal end of the bore has a slightly larger diameter than the second or intermediate bore, or the third or proximal end of the bore in the central shaft. A locking coil is arranged to mate within the stepped large outer diameter (distal end) of the central shaft. The locking coil has an inner diameter which is slightly smaller than the outer diameter of the main coil extending from the cutter jaw assembly to the handle. The main coil is screwed into the locking coil disposed within the central shaft. A sheath which acts as a strain relief, is disposed distally of the locking coil about the main coil within the central shaft. The sheath holds the locking coil within the first stepped bore in the central shaft. The strain relief sheath is bonded to the bore of the central shaft. The proximalmost end of the joggled pull wires extend through the proximal end of the main coil and into a thin anti-kink tube in the narrowest third stepped bore in the central shaft. The cross pin fits through a slot at the midpoint of the central shaft. The slot is in communication with the third bore therein. A cross pin mates with the slot across the central shaft. The proximalmost end of the joggled pull wires are locked into an opening in the cross pin. The ends of the cross pin mate with slots in the spool so as to facilitate corresponding motion in the joggled pull wires.

Proximal movement of the spool with respect to the central shaft effectuates a pull on the joggled pull wires so as to create a pivotable motion of the tangs on the proximal end of the cutters, to cause the cutter jaws to engage to one another. When the pull wires are pulled proximally, however, the coil is compressed.

Movement of the spool distally with respect to the central shaft effectuates a compression on the pull wire thus causing arcuate movement of the tangs on the proximal end of each jaw to force a pivoting motion about the clevis pin thus opening the respective jaws. When the pull wire is compressed or pushed distally, however, the coil is in tension.

Additional objects and advantages of the invention will become apparent to those skilled in the art upon reference to the detailed description taken in conjunction with the provided figures.

DETAILED DESCRIPTION OF THE PREFERRED EMBODIMENT

Figure 1:
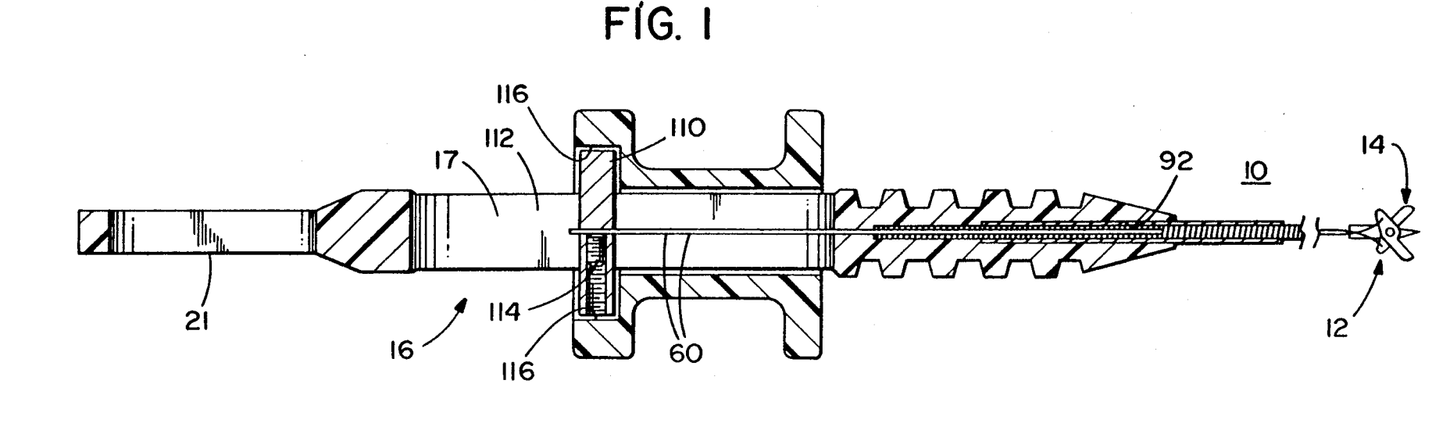
FIG. 1 is a side elevational view in section, of a biopsy forceps assembly.
Figure 2:
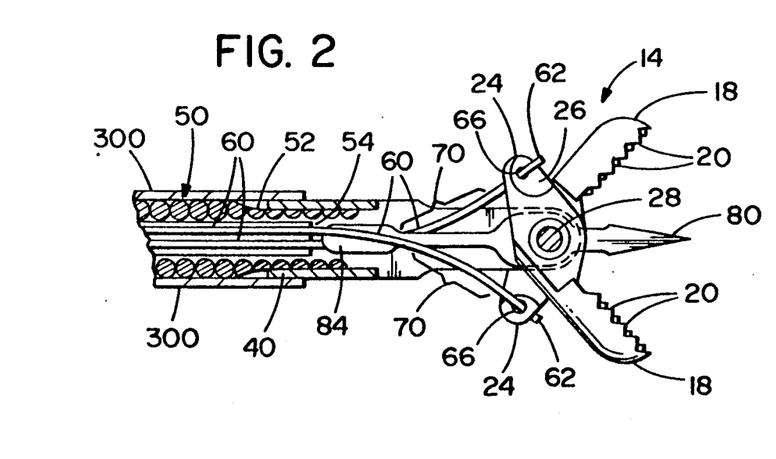
FIG. 2 is a side elevational view of the distalmost end of the preferred biopsy forceps assembly of the invention with a needle, with its cutter jaws being opened.
Figure 3:
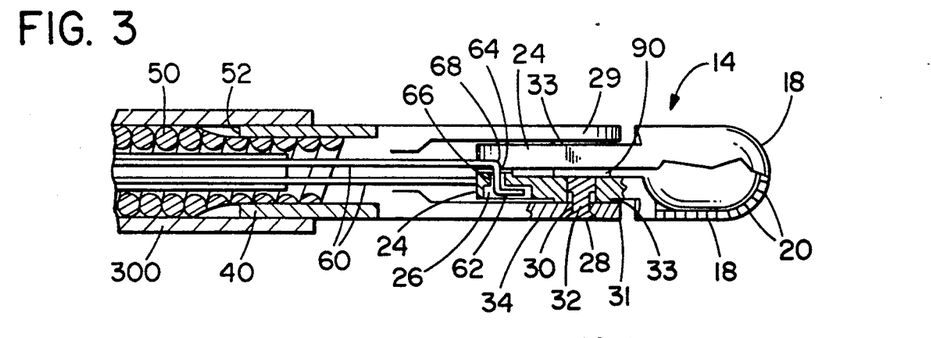
FIG. 3 is a plan view, partly in section, of the distal end of the preferred biopsy forceps of the invention without a needle.
Figure 4:
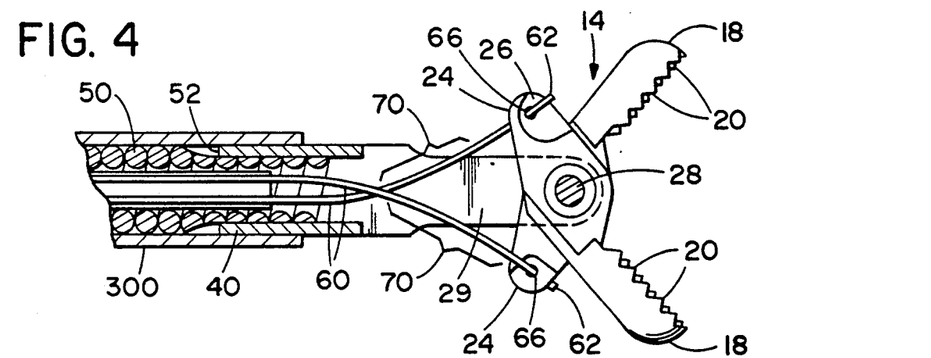
FIG. 4 is a side elevational view partly in section of the biopsy forceps shown in FIG. 3 with its jaws opened.
Figure 5:
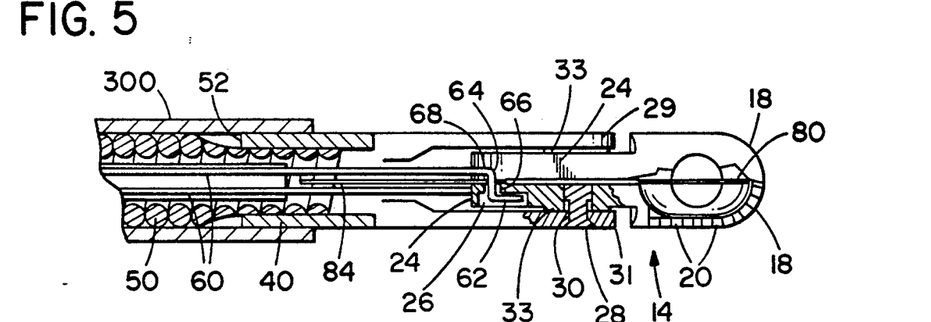
FIG. 5 is a plan view, partly in section, of the distal end of the biopsy forceps assembly, with a needle.

Referring now to the drawings in detail and particularly to FIG. 1, there is shown a biopsy forceps assembly 10, having a distal end 12, comprising a jaw assembly 14, and a proximal end 16 comprising a handle 17, spool 19 and thumb ring 21 for manipulation of the assembly. The jaw assembly 14 comprises a pair of jaws 18, each of which is a duplicate of the other. Each jaw 18 as may be seen in FIGS. 2 and 3, is a generally elongated somewhat hemispherically shaped structure having a distalmost end and a proximalmost end. Each jaw 18 has on its distalmost end, an array of teeth 20 generally radially directed about a point "R", as exemplified in FIG. 3. Each jaw 18 has a generally longitudinal centerline as may be seen in FIGS. 3 and 5. The teeth 20 on one side of the longitudinal centerline of each jaw 18 are displaced by one half pitch from the corresponding teeth 20 on the other side of the longitudinal centerline on that jaw 18. The displacement by one half pitch by the teeth on one side of the jaw 18 is relative to those corresponding teeth 20 on the other longitudinal side of the jaw 18 permits the same casting to be used for both the upper and lower jaws of the jaw assembly 14. The radial arrangement of the teeth 20 as best seen in FIGS. 3 and 5 require each jaw 18 when they close onto one another to automatically mate and effectuate proper alignment therebetween. The self-alignment permits each jaw 18 to be manufactured by an investment casting technique which is inherently less expensive than the typical prior art jaws which are machined and where the distalmost teeth are either non-existant or they are transverse to the longitudinal centerline the jaws, which jaws inherantly fail to have any positive cutting edge at their distalmost ends. The casting of each jaw 18 also permits a looser tolerance therebetween which is characteristic of the casting manufacturing technique without any loss in effectiveness of those jaws.

Each jaw 18 has a proximalmost end which comprises a tang 24. Each tang 24 has a generally semicircular recess position 26 on its outer side thereof. The recessed portion 26 may be seen most clearly in FIGS. 3 and 5, and then a side view in FIGS. 2, 4 and 6. A bore 30 extends transversely through the midpoint between the distal and proximalmost ends of each jaw 18. Each jaw 18 is mated with one another and so as to each be levered about a clevis pin 28 which extends through the bore 30 on each respective jaw 18. Each jaw 18 has an annular boss 33 disposed about the outer face of its bore 30, as shown in FIGS. 3 and 5. The boss 33 acts as a bearing surface to reduce the typical friction found on prior art forceps. The clevis pin 28 is received in a hole 32 in clevis 34 as shown in FIGS. 3 and 5. The clevis 34 extends proximally, as shown in FIGS. 2-6, into a hub 40. The clevis 34, the hub 40 and clevis pin 28 are made from a common casting. The clevis pin 28 unitarily extending from one of the sidearms 29 of the clevis 34.

Figure 8:
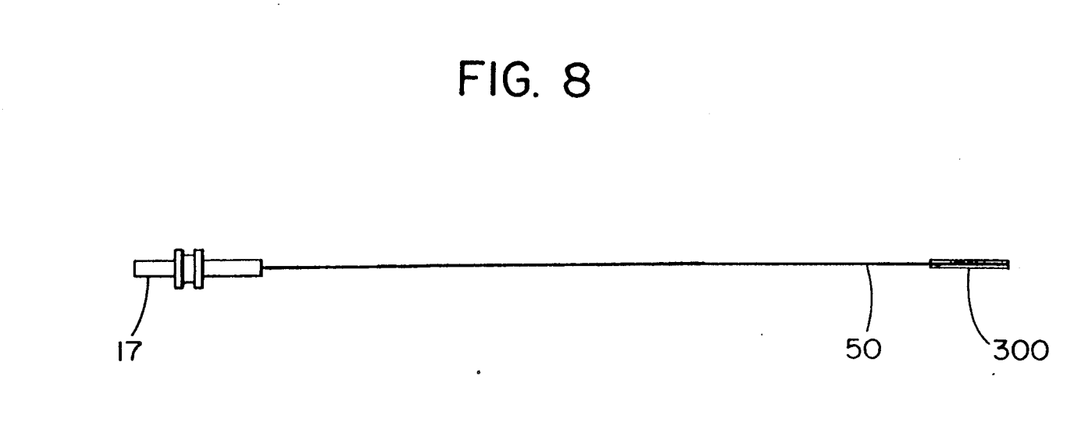
FIG. 8 is an illustration of the coil of the biopsy forceps device of FIG. 1 with a longitudinally scaled segment of the distal end of the coil stiffened.

A main tubular coil 50 shown in FIG. 2 at its distal end thereof, has a portion of it periphery ground flat, as at 52. The flattened distal periphery of the main coil 50 permits a more solid anchoring between the inside of the clevis hub 40 and the distal end of the main coil 50 when the two are crimped together, obviating the need for adhesives, soldering or welding. In the preferred embodiment of the invention, the main coil 50 is a comprised of a stainless steel rod of approximately 0.021 inch diameter which is tightly wound and preloaded into a main coil having an outer diameter of approximately 0.08 inches and a length of approximately seven feet. As seen in FIGS. 2-6, the distal end of the main coil 50 as well as a portion of the clevis hub 40 are covered by a stiffening mechanism 300. The preferred stiffening mechanism 300 is a Teflon FEP shrink wrap tube which is approximately eight inches in length (although other lengths can be utilized). The relative lengths of the coil 50 and stiffening coating 300 are seen in FIG. 8. The shrink wrap tubing typically has a diameter of approximately 0.085 inches and a typical wall thickness of about 0.005 inches. When heated to approximately three hundred eighty degrees Fahrenheit, the shrink wrap tubing shrinks over the coil and clevis hub and desirably stiffens the distal end of the coil 50 relative to the uncovered main part of the coil. Although the distal end of the main coil is stiffer than would be otherwise, damage to the endoscope through which the biopsy forceps device is inserted is avoided, as the shrink wrap is lubricious and smooth.

Figure 9:
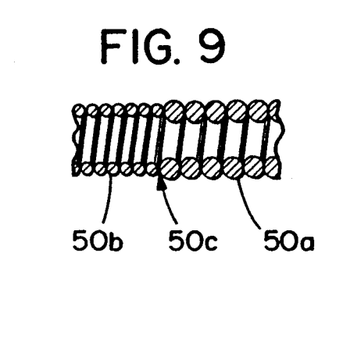
FIG. 9 is an illustration of a spliced coil for use with the biopsy forceps device of FIG. 1.

If desired, in order to obtain a stiffer distal end, instead of covering the main coil 50 with the Teflon shrink tube stiffening mechanism 300, a stiffer stainless steel material 50a may be spliced at 50c to a less stiff stainless material 50b, all as seen in FIG. 9, such that the distal end of the coil is stiffer than the main portion of the coil 50. While a spliced coil provides the desired stiffness, it is not preferred, as it does not provide additional lubricity and smoothness to offset the disadvantages which accompany the stiffness.

Figure 7:
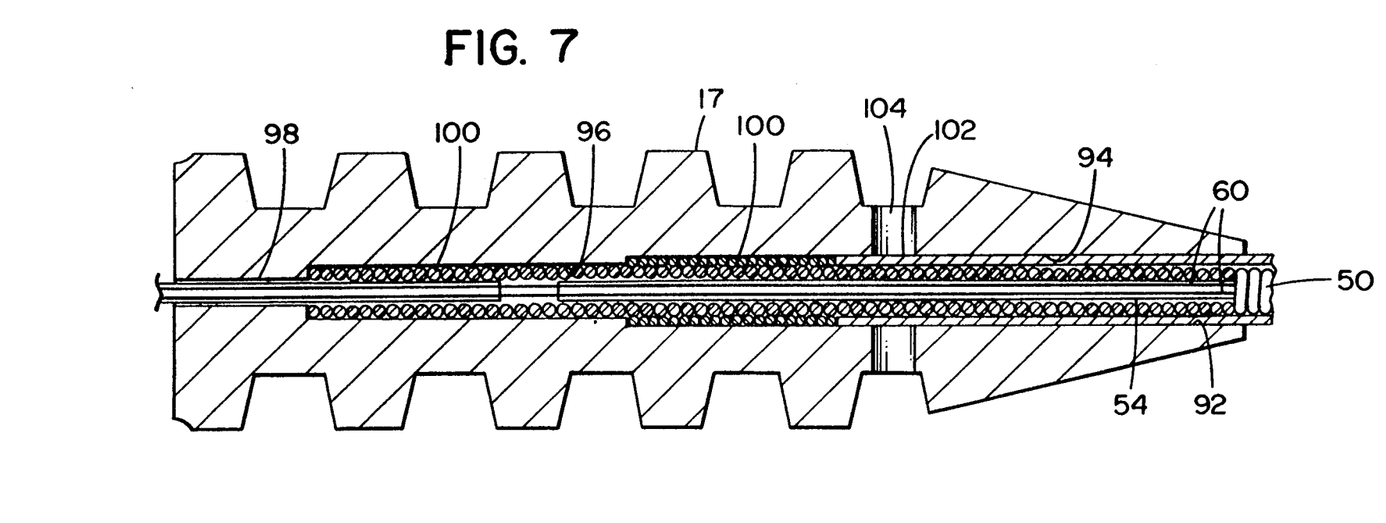
FIG. 7 is a side elevational view in section, showing part of the handle at the proximalmost end of the preferred biopsy forceps assembly.

A polyethylene sheath 54 extends from the distal end of the main coil 50 therethrough into the central shaft 56 of the handle 17 as shown in FIGS. 2 and 7. This sheath 54 acts as a bearing between a pair of pull wires 60 and the lumen of the main coil 50.

The distalmost end of each pull wire 60 has a Z-bend therein. The Z-bend of each pull wire 60 has a first portion 62 which is rotatably disposed in the recess 26 in the tang 24 of each cutter jaw 18. The Z-bend has a second portion 64 which extends through a bore 66 in the proximalmost end of the tang 24, as best shown in FIGS. 3 and 5. A ninety degree bend 68 between the second portion 64 and the main pull wire 60 eliminates the pinching common to prior art loop design wires. Each pull wire 60 has a reflex curve 70 as shown in FIG. 2 as well as in FIGS. 6 and 7, extending between their distalmost ends and the distalmost end of the main coil 50. The reflex curve 70 helps to open the cutter jaws 18 when the spool 19 on the handle 17 is displaced distally thereto.

Figure 6:
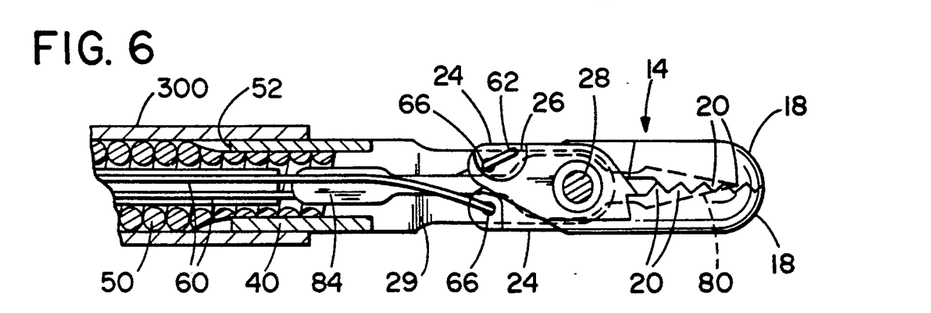
FIG. 6 is a side elevational view partly in section, of the biopsy forceps shown in FIG. 5.

FIGS. 2, 5 and 6 show the distal end of the biopsy forceps assembly 10 with a flat needle 80 disposed between the two cutter jaws 18. The needle 80 has a pointed distalmost end 82 that terminates just within the cutter jaws 18 when closed, and has tail 84 comprising its proximalmost end which extends within the distalmost end of the main coil 50. The needle 80 has a central opening through which the clevis pin 28 may extend as shown in FIGS. 3 and 5. The needle 80 is flat, and as such may be disposed between the two tangs 24 of each cutter jaw 18 as shown in FIG. 5. In cutter jaw assembly 14 without the needle therein, a washer 90 is disposed between the two cutter jaws 18 on the clevis pin 28.

The proximal end of the main coil 50 and the proximal end of the pull wires 60 extend into handle 17 at the proximal end 16 of the biopsy forceps assembly 10. The handle 17 comprises a central shaft about which a displaceable spool 19 is disposed. The central shaft has a longitudinally directed stepped diameter bore 92 extending therein, as shown in FIGS. 1 and 7. The proximal end of the main coil 50 extends into the bore 92 on the proximal end of the central shaft. The bore 92 extending into the central shaft has a three stepped configuration. The bore 92 on the distalmost end of the central shaft has a large first diameter 94 as shown in FIG. 7 which steps to a smaller second diameter 96 which subsequently steps down to a smaller yet third diameter bore 98. A locking coil 100 is disposed against the first largest diameter bore 94 in the central shaft. The main coil 50 has an outer diameter slightly larger than the inner diameter of the locking coil 100 and is threadedly received therethrough. The main coil 50 thus extends to and abuts the handle 17 adjacent the second stepped bore 96 of the bore 92 in the central shaft. The pull wires 60 disposed through the inner lumen of the main coil extend therethrough and into the smallest portion 98 of the bore 92 in the central shaft. A strain relief sheath 102 is disposed distally to the locking coil about the main coil 50 within the largest bore 94 in the central shaft. The strain relief sheath 102 extends slightly distally of the distalmost end of the central shaft, and is bonded to the inner walls of the largest bore 94 by a solvent which is directed thereto through a hole 104, as shown in FIG. 7. The strain relief sheath 102 limits twist and movement of the main coil 50 with the bore 94 while preventing a sharp bend of the coil 50 at the distal end of the handle 17. The proximalmost end of the pull wires 60 extend through the proximal end of the main coil 50 as aforementioned and through and anti-kinking tube 109, and are locked into a cross pin 110, as shown in FIG. 1, which cross pin 110 mates with a slot 112 disposed across the central shaft of the handle 17. The slot 112 is in communication with the axial bore 92 in the central shaft. The proximalmost end of the pull wires 60 are locked into the cross pin 110 by a set screw 114 as shown in FIG. 1. The ends of the cross pins 110 mate with a slot 116 in the spool so as to lock the cross pin 110 therewith. Movement of the spool 19 which is disposed about the central shaft thereby effectuates movement of the puller wires 60 disposed within the main coil 50, the distal ends of which are attached to the tangs 24 on the cutter jaws 8 as shown in FIGS. 1 and 2.

The aforedescribed biopsy forceps assembly are made in a very cost effective manner. The cutter jaws and clevis of the biopsy forceps are made of a cast material which permits of a far less expensive manufacture because of its simplicity. In fact, the casting allows for a single jaw design having self-aligning radially directed distal jaw teeth which are extremely effective in cutting and are easily assembled. The pull wire arrangement with each particular jaw eliminates the prior art multiple linkages which have frictional problems and potential for breakage therewith. The spool design for the grasping of the pull wires in regard to the handle therewithin facilitates a one-handed operation thus permitting the physician use of his other hand for other purposes.

There have been described and illustrated herein biopsy forceps devices. While particular embodiments of the invention have been described, it is not intended that the invention be limited exactly thereto, as it is intended that the invention be as broad in scope as the art will allow. Thus, while exact dimensions and specifics regarding the stainless steel coil and the shrink wrap tubing were provided, it will be appreciated that other stainless steel and shrink wrap tubing having different dimensions and particulars may be utilized. All that is required to practice the invention is to provide a biopsy forceps device where the distal end of the flexible main coil is stiffer than the main portion (i.e., the majority) of the main coil. Also, while two manners of stiffening the distal end of the main coil was described (shrink wrap tubing, and splicing a different material to the coil), it will be appreciated that other stiffening mechanisms could be utilized, such as, by way of example and not by way of limitation, treating the distal end of the coil chemically. Therefore, it will be apparent to those skilled in the art that other changes and modifications may be made to the invention as described in the specification without departing from the spirit and scope of the invention as claimed.

We claim:

1. A biopsy forceps device for the taking of a biological tissue sample from a body, comprising:
   a) a flexible main coil having distal and proximal end portions, with said distal end portion of said main coil having stiffening means for making said distal end portion stiffer than a majority of said flexible main coil;
   b) opposed first and second jaws coupled to said distal end portion of said main coil, with at least one of said first and second jaws being hingedly coupled to said distal end portion;
   c) coupling means for coupling said opposed first and second jaws with said distal end portion of said flexible main coil, wherein said coupling means has a proximal end and a distal end, and said proximal end of said coupling means contacts said distal end portion of said flexible main coil, and said stiffening means extends proximally of said proximal end of said coupling means; and
   d) actuation means having a distal end coupled to each said hingedly coupled jaw, said actuation means for effecting articulation of each hingedly coupled jaw.

2. A biopsy forceps device according to claim 1, wherein:
said stiffening means comprises shrink wrap tubing coaxially surrounding said distal end portion of said main coil and moving one end terminating thereon.

3. A biopsy forceps device according to claim 2, wherein:
said shrink wrap tubing is more lubricious and smooth than said flexible main coil.

4. A biopsy forceps device according to claim 3, wherein:
said shrink wrap tubing comprises Teflon FEP tubing.

5. A biopsy forceps device according to claim 4, wherein:
said shrink wrap tubing is approximately eight inches long.

6. A biopsy forceps device according to claim 4, wherein:
each said opposed first and second jaws is substantially hollow to permit the taking of a biological tissue sample.

7. A biopsy forceps device according to claim 2, wherein:
said first and second jaws are both hingedly coupled to said distal end of said main coil, and
said biopsy forceps device further comprises,
   e) a handle means for handling the clevice disposed on said proximal end of said main coil, wherein said coupling means comprises a clevis having a pivot in said distal end of said coupling means, said opposed first and second jaws being coupled to said pivot and pivoting thereabout, and said proximal end of said coupling means being coupled to said distal end of said main coil, wherein said shrink wrap tubing covers said proximal end of said coupling means.

8. A biopsy forceps device according to claim 7, wherein:
said shrink wrap tubing is more lubricious and smooth than said flexible main coil.

9. A biopsy forceps device according to claim 8, wherein:
said shrink wrap tubing is approximately eight inches long.

10. A biopsy forceps device according to claim 7, wherein:
said actuation means comprises first and second pull wires disposed in said main coil, said first and second pull wires having proximal and distal ends, with said proximal ends of said first and second pull wires coupled to said handle means, and with said distal ends of said first and second pull wires respectively coupled to said opposed first and second jaws.

11. A biopsy forceps device according to claim 10, wherein:
each said opposed first and second jaws is substantially hollow to permit the taking of a biological tissue sample.

12. A biopsy forceps device according to claim 1, wherein:
said stiffened distal end portion of said main coil is approximately eight inches long.

13. A biopsy forceps device according to claim 1, wherein:
said distal end of said coil is comprised of a stainless steel coil having a first stiffness, and the remainder of said coil is comprised of a stainless steel coil having a second stiffness, wherein said first stiffness is greater than said second stiffness, and said stainless steel coil having said first stiffness is spliced to said stainless steel coil having said second stiffness.

14. A biopsy forceps device according to claim 13, wherein:
each said opposed first and second jaws is substantially hollow to permit the taking of a biological tissue sample.

15. A biopsy forceps device according to claim 1, wherein:
each said opposed first and second jaws is substantially hollow to permit the taking of a biological tissue sample.

16. A biopsy forceps device according to claim 12, wherein:
each said opposed first and second jaws has a distal portion having a substantially semicircular rim, said substantially semicircular rim having a radial array of substantially triangular cutting teeth extending regularly therefrom, wherein said radial array of substantially triangular cutting teeth of said opposed first jaw extend toward said radial array of substantially triangular cutting teeth of said opposed second jaw and said substantially triangular cutting teeth of said opposed first jaw closely mesh with said triangular cutting teeth of said opposed second jaw when said opposed first and second jaws are in a closed position.

17. A biopsy forceps device according to claim 16, wherein:
said opposed first and second jaws are identical.

18. A biopsy forceps device according to claim 17, wherein:
said first and second jaws each have a longitudinal centerline, and for each jaw, said substantially triangular teeth on a first side of said longitudinal centerline are displaced by one half pitch from corresponding teeth on a second side of said longitudinal centerline.

19. A biopsy forceps device according to claim 16, wherein:

said opposed first and second jaws further comprise a generally rear portion having a parallel line rim extending from said semicircular rim, said parallel line rim having a second array of substantially triangular teeth extending therefrom, wherein said second array of substantially triangular teeth of said opposed first jaw extend toward said second array of substantially triangular teeth of said opposed second jaw.

20. A biopsy forceps device according to claim 19, wherein:

said opposed first and second jaws are identical, and said first and second jaws each have a longitudinal centerline, and for each jaw, said substantially triangular teeth of said first and second arrays on a first side of aid longitudinal centerline are displaced by one half pitch from corresponding teeth of said first and second arrays on a second side of said longitudinal centerline.

* * * * *

UNITED STATES PATENT AND TRADEMARK OFFICE
CERTIFICATE OF CORRECTION

PATENT NO. : 5,228,451

DATED : July 20, 1993

INVENTOR(S) : Thomas O. Bales, Matthew A. Palmer and Jeff A. Wilson

It is certified that error appears in the above-identified patent and that said Letters Patent is hereby corrected as shown below:

Column 7, line 35
    replace "moving" with --having--.

Signed and Sealed this

Fifth Day of April, 1994

*Attest:*

BRUCE LEHMAN

*Attesting Officer*     *Commissioner of Patents and Trademarks*